United States Patent
Green et al.

(10) Patent No.: US 7,101,333 B2
(45) Date of Patent: *Sep. 5, 2006

(54) METHODS AND APPARATUS FOR LOADING RADIOACTIVE SEEDS INTO BRACHYTHERAPY NEEDLES

(76) Inventors: Thomas C. Green, 11071 Arroyo Beach Pl., SW., Seattle, WA (US) 98146; Michael J. Horzewski, 6032 Running Springs Rd., San Jose, CA (US) 95135; Jason Klofstad, Bldg. 220, P.O. Box 29450, San Francisco, CA (US) 94129-0450

(*) Notice: Subject to any disclaimer, the term of this patent is extended or adjusted under 35 U.S.C. 154(b) by 0 days.

This patent is subject to a terminal disclaimer.

(21) Appl. No.: 10/693,598

(22) Filed: Oct. 23, 2003

(65) Prior Publication Data

US 2004/0087828 A1 May 6, 2004

Related U.S. Application Data

(63) Continuation of application No. 09/998,610, filed on Nov. 29, 2001, now Pat. No. 6,638,206, which is a continuation of application No. 09/522,248, filed on Mar. 9, 2000, now Pat. No. 6,358,195.

(51) Int. Cl.
*A61M 36/00* (2006.01)
*A61M 5/00* (2006.01)

(52) U.S. Cl. .......................................................... 600/7

(58) Field of Classification Search .................. 600/1–8
See application file for complete search history.

(56) References Cited

U.S. PATENT DOCUMENTS

| | | | |
|---|---|---|---|
| 4,086,914 A | 5/1978 | Moore | |
| 4,167,179 A | 9/1979 | Kirsch | |
| 4,700,692 A | 10/1987 | Baumgartner | |
| 4,815,449 A | 3/1989 | Horowitz | |
| 5,460,592 A | 10/1995 | Langton et al. | |
| 5,928,130 A | 7/1999 | Schmidt | |
| 6,036,631 A | 3/2000 | McGrath et al. | |
| 6,083,166 A | 7/2000 | Holdaway et al. | |
| 6,213,932 B1 | 4/2001 | Schmidt | |
| 6,358,195 B1 | 3/2002 | Green et al. | |
| 6,638,206 B1 * | 10/2003 | Green et al. | 600/7 |

FOREIGN PATENT DOCUMENTS

WO  WO 99/20337  4/1999

* cited by examiner

*Primary Examiner*—John P. Lacyk

(57) ABSTRACT

Methods and apparatus are provided for loading therapeutic materials into brachytherapy needles. The apparatus comprises a loading tube with a lumen and two transverse slots, and radioactive seed and spacer cartridges slidably received within the transverse slots. The apparatus may be used in conjunction with a standard brachytherapy plunger and needle coupled to, respectively, the proximal and distal ends of the loading tube. The plunger dislodges seeds and spacers from the cartridge chambers to load the needle with a predetermined packing arrangement.

20 Claims, 4 Drawing Sheets

METHODS AND APPARATUS FOR LOADING RADIOACTIVE SEEDS INTO BRACHYTHERAPY NEEDLES

FIELD OF THE INVENTION

This invention relates to improved apparatus and methods for the treatment of prostate cancer. More particularly, the present invention provides improved methods and apparatus for loading radioactive seeds into brachytherapy needles.

BACKGROUND OF THE INVENTION

Excluding nonmelanoma skin cancers, prostate cancer is the most common cancer afflicting American men. The American Cancer Society estimates that over 180,00 new cases will be diagnosed in the U.S. in the year 2000 alone, and that nearly 32,000 people will die from the disease. Prostate cancer is second only to lung cancer as the leading cause of cancer death in men, accounting for roughly 11%.

Prostate cancer is defined as malignant tumor growth within the prostate gland. Its cause is unknown, although high dietary fat intake and increased testosterone levels are believed to be contributory factors. A letter scale ("A" through "D"), which accounts for the location of the cancer, is commonly used to classify the stage of disease. In Stage A, the tumor is not palpable but is detectable in microscopic biopsy. Stage B is characterized by a palpable tumor confined to the prostate. By Stage C, the tumor extends locally beyond the prostate with no distant metastasis. By Stage D, cancer has spread to the regional lymph nodes or has produced distant metastasis.

In the early stages, prostate cancer is most commonly treated by prostate removal or by brachytherapy. More advanced cases are treated by medical hormonal manipulation or orchiectomy to reduce testosterone levels and curb spreading of the disease, by chemotherapy, or by external beam radiation therapy.

With regard to treatment of early stage prostate cancer, the state of the art has several drawbacks. Radical prostatectomy is often recommended for treatment of localized stage A and B prostate cancers. Under general or spinal anesthesia, an incision is made through a patient's abdomen or perineal area, and the diseased prostate is removed. The procedure is lengthy, especially if a lymph node dissection is simultaneously performed, and requires a hospital stay of 2–5 days. Possible complications include impotence and urinary incontinence.

Internal radiation therapy or brachytherapy has recently been modified and holds great promise for the treatment of early stage prostate cancer. Radioactive pellets or seeds of, for example, iodine-125, gold-198, palladium-103, ytterbium-169, or iridium-192, are deposited directly into the prostate through needle placement. Imaging tests, such as transrectal ultrasound, CT scans, or MRI, are used to accurately guide placement of the radioactive material. Advantageously, radiation is administered directly to the prostate with less damage to surrounding tissues, requiring a significantly smaller radiation dosage as compared to external beam radiation therapy. Furthermore, the procedure need only be performed once. Complications include a lower, yet still significant, incidence of impotence and urinary incontinence, compared to prostate removal procedures.

The radioactive seeds are placed inside thin needles, which are inserted through the skin of the perineum (area between the scrotum and anus) into the prostate. Each needle is slowly retracted with a spinning motion by a first practitioner while a plunger within the needle, and proximal of the radioactive seeds, is held stationary by a second practitioner. The plunger keeps the seeds in place during retraction of the needle, while rotation of the needle during retraction prevents jamming of the seeds while delivering the seeds in a line within the prostate.

The seeds, which are permanently implanted, give off radiation for weeks or months. Their presence causes little discomfort, and they are left in the prostate after decay of the radioactivity. For about a week following needle insertion, patients may experience pain in the perineal area, and urine may have a red-brown discoloration.

Current surgical apparatus and methods for loading the seeds into the brachytherapy needles prior to delivery are both hazardous and inefficient. Medical personnel hand-load the seeds in an alternating arrangement of seeds and spacers, thereby unnecessarily subjecting the personnel to radiation exposure. Minute seed size (e.g., 5 mm in length) compounds the problem by making the procedure slow and meticulous. Furthermore, the seeds accidentally may be dropped or misplaced during loading, thereby increasing exposure risk. Also, the seed loader may make a mistake in the packing order of seeds and spacers, potentially leading to "hot spots" and "cold spots" within a patient's prostate where the tissue is subjected to incorrect radiation dosages. Finally, the types and total number of seeds and needles used must be individualized for each patient depending on the size of the prostate and the Gleason score of the cancer, thereby increasing opportunity for error.

Attempts have been made to address various aspects of these concerns. For example, U.S. Pat. No. 4,815,449 to Horowitz describes an absorbable member with seeds spaced within the member to facilitate proper spacing during delivery. The absorbable member may be pre-formed for easy loading. While pre-forming may effectively decrease the complexity and time required to load the needles, it also impedes the physician's ability to tailor the seed spacing to a specific patient's needs. Furthermore, these absorbable members have been prone to jamming within the needle in clinical use.

U.S. Pat. No. 5,928,130 to Schmidt provides a sleeve, pre-loaded with seeds and spacers at a remote site, which may be inserted through the needle lumen. Seeds then are implanted using conventional techniques. As with the Horowitz device, the physician's ability to tailor seed spacing is limited. Furthermore, the method of loading seeds into the sleeve at the remote site is not disclosed, and presumably involves technicians at the loading site being exposed to radiation.

PCT publication WO 99/20337 to Rydell describes a gun-like radioactive seed implantation device that strips seeds one by one from a cartridge and advances them to the implantation site. The Rydell device has several drawbacks. The device is rather large and may prove intrusive in the surgical field. It increases the time required to perform surgery since seeds only may be delivered one at a time. The device also is mechanically complex and may be subject to malfunction. Finally, there is only one cartridge from which the device draws implantable materials. Thus, a packing arrangement of seeds and spacers tailored for a specific patient requires pre-loading of the cartridge, again exposing the loader to radiation.

While each of these devices may provide some benefit over the previously known apparatus and methods, none satisfactorily addresses the shortcomings of current loading techniques. In view of these drawbacks, it would be desirable to provide methods and apparatus that allow rapid seed loading.

It further would be desirable to provide methods and apparatus for brachytherapy seed loading that minimize radiation exposure of attendant medical personnel.

It also would be desirable to provide methods and apparatus that may be used in conjunction with standard brachytherapy needles.

It further would be desirable to provide methods and apparatus that allow tailoring of the packing arrangement of seeds and spacers to meet the needs of a specific patient.

SUMMARY OF THE INVENTION

In view of the foregoing, it is an object of the present invention to provide methods and apparatus for brachytherapy seed loading that allow rapid seed loading.

It is also an object of the present invention to provide methods and apparatus that minimize radiation exposure of attendant medical personnel.

It is another object of this invention to provide methods and apparatus that may be used in conjunction with standard brachytherapy needles.

It is a further object of the present invention to provide methods and apparatus that allow tailoring of the packing arrangement of seeds and spacers to meet the needs of a specific patient.

These and other objects of the present invention are accomplished by providing methods and apparatus for brachytherapy seed loading comprising a tube with two detachable loading cartridges. One cartridge dispenses radioactive seeds; the other dispenses spacers. When used in conjunction with a standard brachytherapy needle and plunger, the present invention allows quick and easy loading of tailored seed delivery profiles, and reduces radiation exposure of medical personnel.

In a preferred embodiment, a distal end of the tube lumen is in communication with a lumen of the brachytherapy needle. The plunger is inserted in a proximal end of the tube lumen. The loading cartridges are in communication with the tube lumen, and the plunger may be advanced to controllably dislodge seeds or spacers from the cartridges, which are then gravity-fed into the needle lumen. In an alternative embodiment, a specialized plunger may be used in place of the standard brachytherapy plunger to strip seeds/spacers from the cartridges.

Methods of using the present invention also are provided.

BRIEF DESCRIPTION OF THE DRAWINGS

Additional objects and advantages of the invention will be apparent from the following description, the accompanying drawings and the appended claims, in which:

DETAILED DESCRIPTION OF THE INVENTION

The present invention provides methods and apparatus for loading radioactive seeds into brachytherapy needles. More particularly, the present invention provides a tube with two loading cartridges filled respectively with seeds and spacers. The seeds and spacers controllably are stripped from the cartridges and loaded into the needles.

Figure 1:
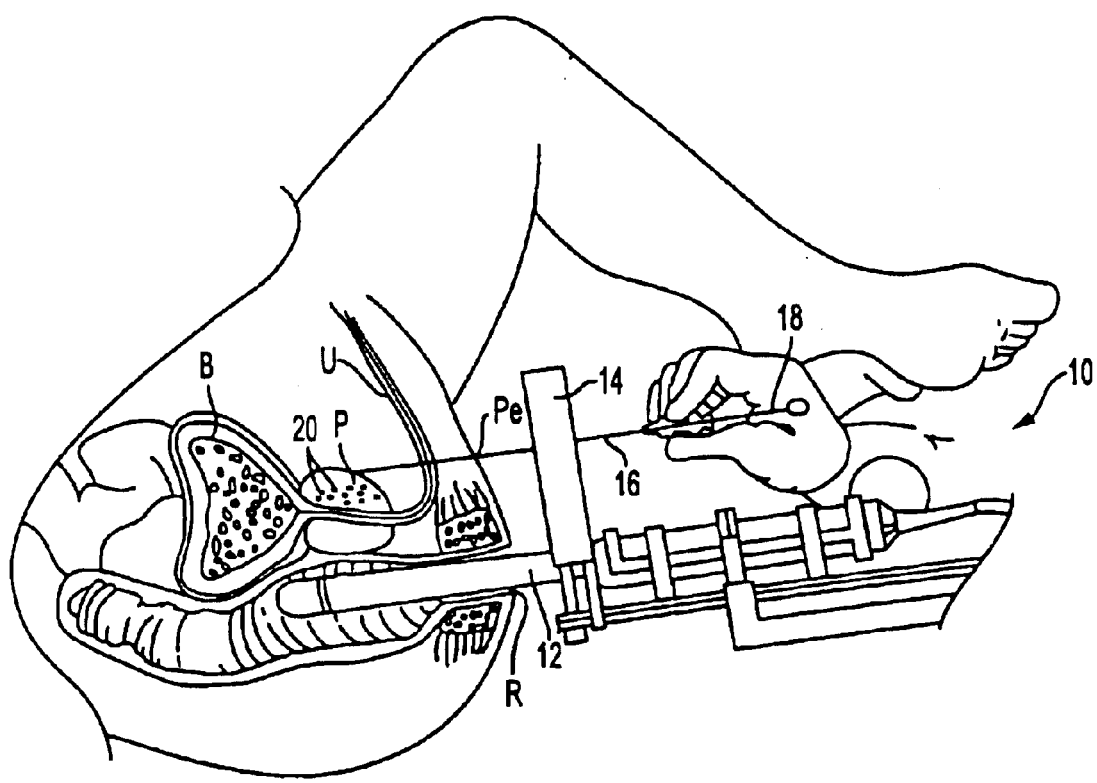
FIG. 1 is a schematic view of a prior art method of performing brachytherapy.

Referring now to FIGS. 1, the prior art method of performing brachytherapy is described. The method and apparatus are as taught by Peter Grimm, DO, in a pamphlet entitled, "Ultrasound Guided Implantation of the Prostate: A Practical Review Course." Brachytherapy apparatus 10 comprises transrectal ultrasound probe 12, guide block 14, needle 16, plunger 18, and radioactive seeds 20. Ultrasound probe 12 is advanced through a patient's rectum R to facilitate imaging of the patient's prostate P. Prostate P surrounds the urethra U and is just proximal of the bladder B. Needle 16, loaded with seeds 20 and plunger 18, is advanced through the patient's perineum Pe into prostate P, where needle 16 is retracted and seeds 20 are delivered to the patient. Radioactive seeds 20 and spacers 22 (see FIG. 2) are commonly loaded into needles 16 by hand, the drawbacks of which are described hereinabove.

Figure 2:
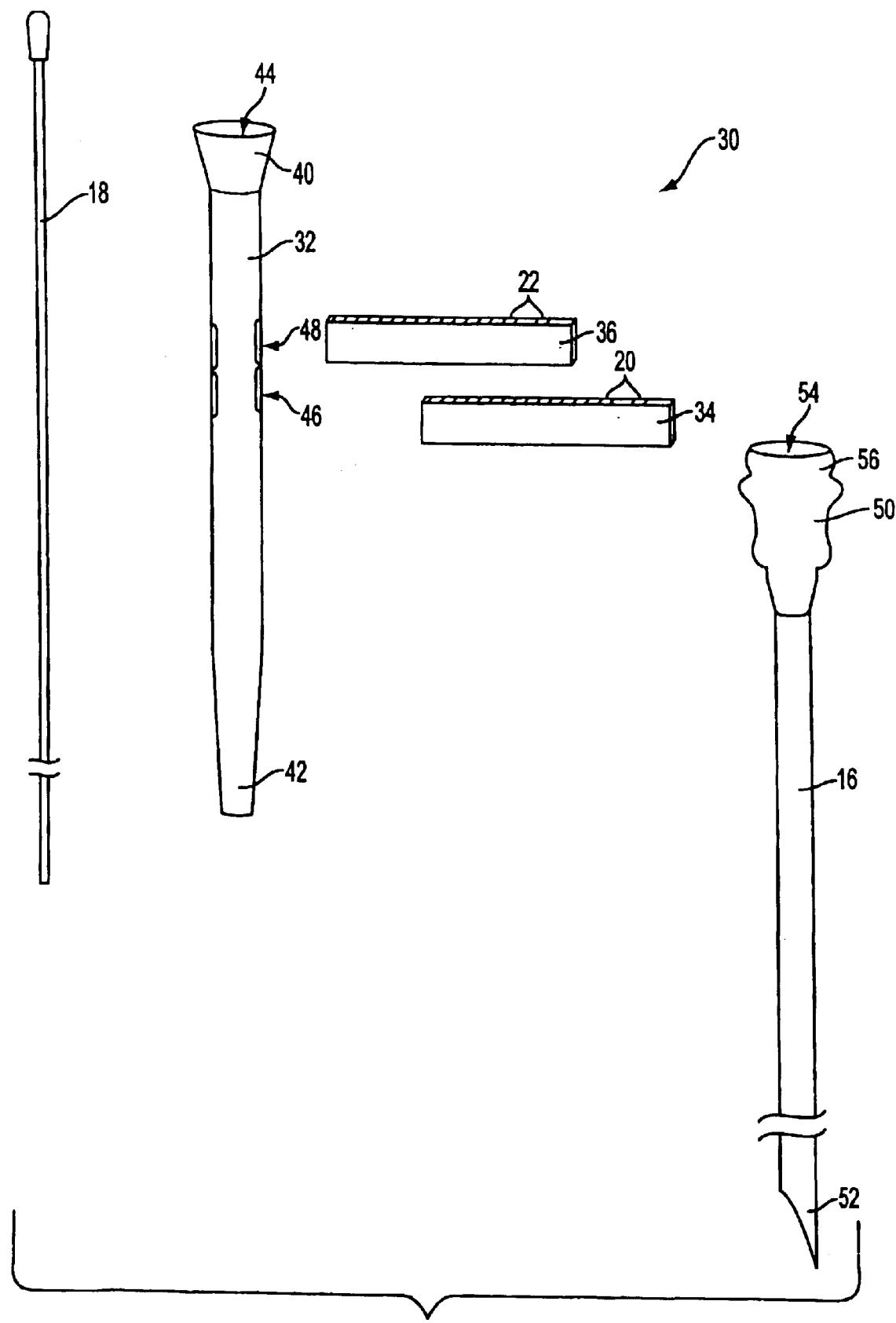
FIG. 2 is an exploded side view of apparatus constructed in accordance with the present invention.

With reference to FIG. 2, apparatus constructed in accordance with the present invention for loading seeds into needles is described. Apparatus 30 comprises loading tube 32, radioactive seed cartridge 34 containing seeds 20, and spacer cartridge 36 containing spacers 22. Apparatus 30 may be used in conjunction with standard brachytherapy needle 16 and plunger 18 of FIG. 1. Loading tube 32 comprises enlarged proximal end 40, tapered distal end 42, and lumen 44 extending therebetween. It further comprises transverse slots 46 and 48 configured to slidably receive cartridges 34 and 36.

Needle 16 comprises proximal end 50, sharpened distal end 52, and lumen 54 extending therebetween. Proximal end 50 comprises hub 56 that facilitates manipulation of the needle. The opening at the distal tip of needle 16 is initially filled with bone wax that melts when placed inside the body. The needle lumen is filled, in an alternating pattern, with seeds 20 and spacers 22. For this purpose, tapered distal end 42 of loading tube 32 is configured to be received in lumen 54 of needle 16, which extends through hub 56. Likewise, plunger 18 is configured to be received in enlarged proximal end 40 of loading tube 32.

Figure 3:
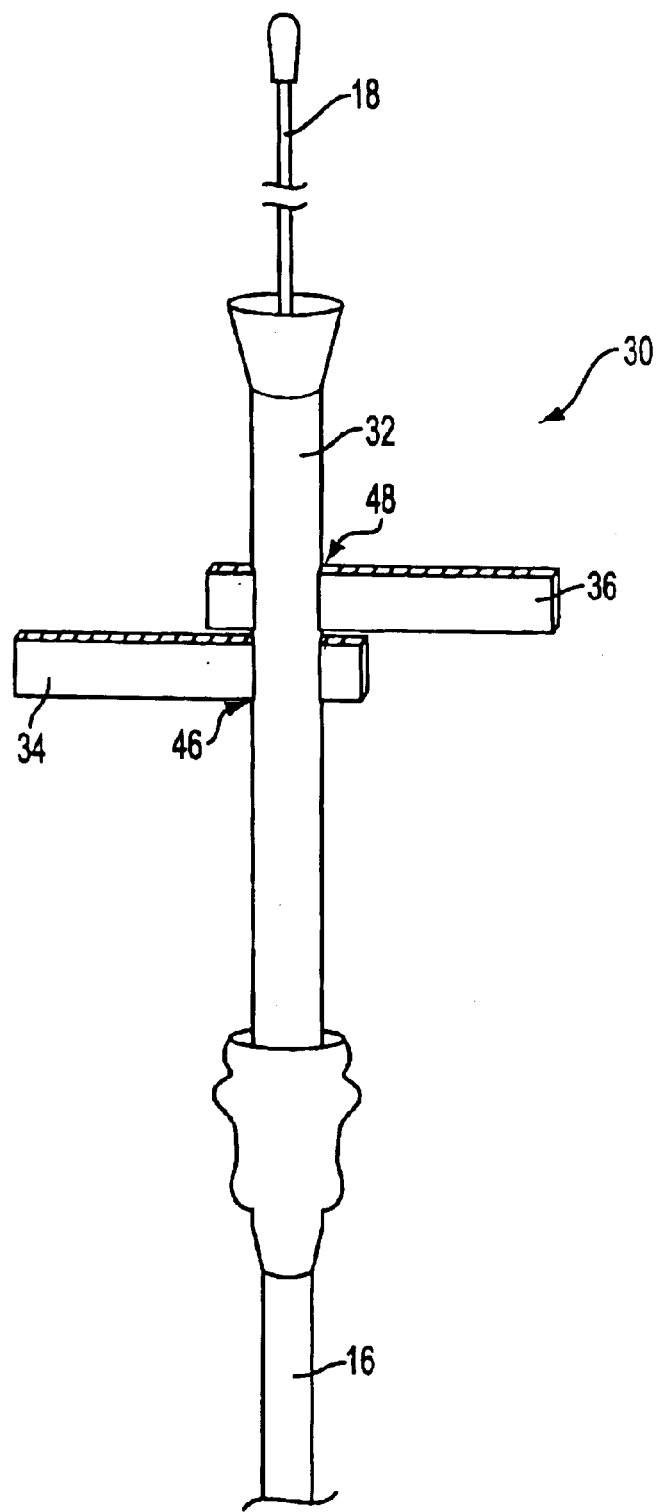
FIG. 3 is an assembled side view of the apparatus of FIG. 2.
Figure 4:
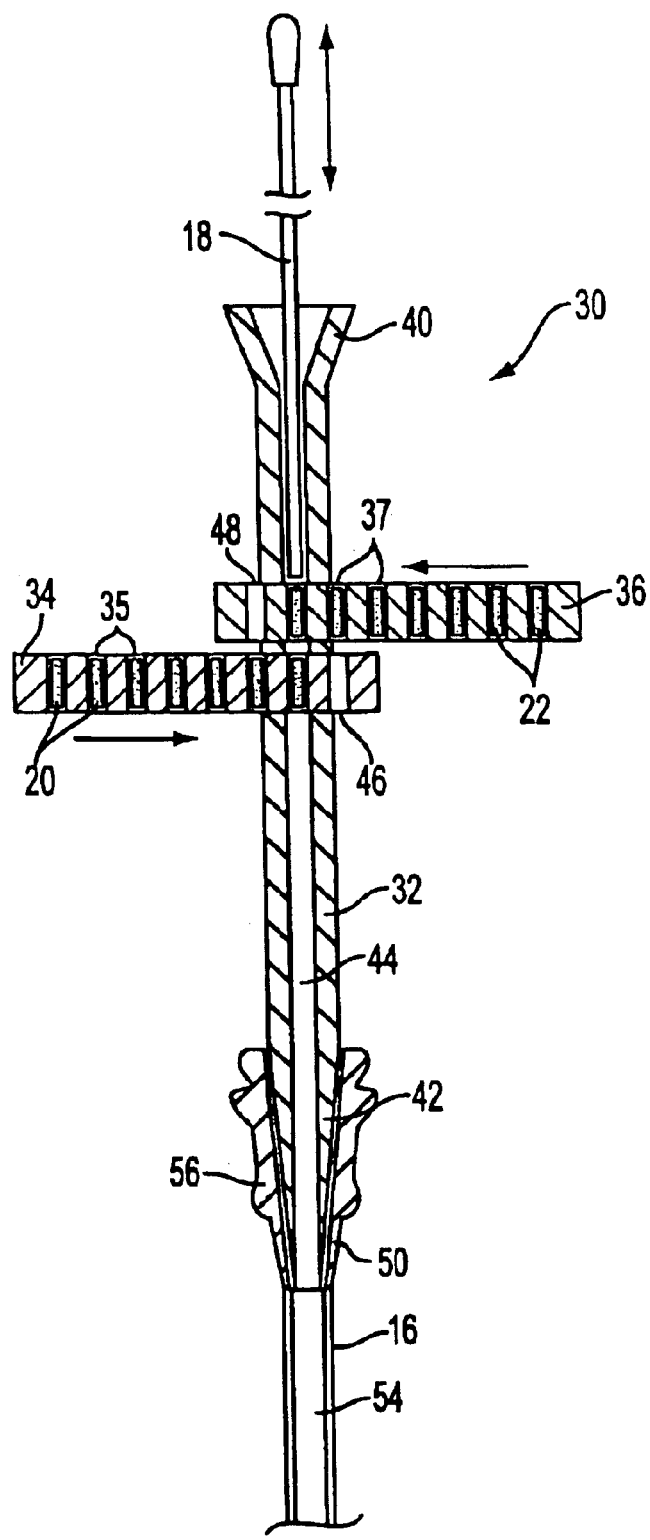
FIG. 4 is a cross-sectional view of the apparatus of FIGS. 2 and 3.

With respect to FIGS. 3 and 4, the apparatus of FIG. 2 is shown assembled for use loading needle 16. Cartridges 34 and 36 are slidably disposed within transverse slots 46 and 48, tube 32 is received within needle 16, and plunger 18 is disposed in tube 32.

Cartridges 34 and 36 each comprise a plurality of chambers 35 and 37, respectively, which are configured to receive seeds 20 and spacers 22, respectively. The seeds and spacers may, for example, be loaded into the chambers by remotely operated machines, so that radiation exposure is mitigated. Alternatively, the seeds or spacers may be press-fit into chambers 35 and 37, or retained within chambers 35 and 37, for example, by bone wax. Cartridge 34 preferably also comprises a shielding material, such as lead. As a further alternative, cartridges 34 and 36 may comprise a transparent or translucent material to facilitate determination of whether the chambers are full or empty.

A method of using apparatus 30 is now described. Tapered distal end 42 of loading tube 32 is received by lumen 54 in hub 56 of needle 16, plunger 18 is disposed in enlarged proximal end 40 of loading tube 32, and the opening at the distal tip of needle 16 is filled with bone wax. Cartridges 34 and 36 are translated within slots 46 and 48 until a first chamber 35 and a first chamber 37 align with lumen 44 of loading tube 32. The distal end of plunger 18 is advanced from the proximal to the distal end of lumen 44, thereby passing through the chamber 35 and the chamber 37 aligned with lumen 44.

If a seed 20 or a spacer 22 is contained, respectively, in the chamber 35 or the chamber 37 aligned with lumen 44, it is forced out of the chamber by distal advancement of plunger 18 and is gravity-fed through lumen 44 into lumen 54 of needle 16. If no seed or spacer is in a chamber aligned with the lumen, plunger 18 passes unencumbered through that chamber. Once a chamber has been emptied, the cartridges may be advanced through slots 46 and 48 to align subsequent filled chambers with lumen 44. Thus, a medical practitioner can load needle 16 with a tailored packing arrangement of seeds 20 and spacers 22 by selectively aligning filled or empty chambers 35 and 37 with lumen 44 of loading tube 32, and distally advancing plunger 18 through the chambers. Alternatively, the positioning of cartridges 34 and 36, as well as actuation of plunger 18, may be controlled by a computer controlled robot, such as are known in the art.

The loading procedure described hereinabove is expected to be efficient and reduce the length of time required to load brachytherapy needles. In addition, the radiation exposure of medical personnel responsible for loading the needles is expected to be reduced. The funnel shape of tapered end 42 is also expected to prevent the jamming commonly seen at the interface of hub 56 and needle 16 during hand loading.

Although particular embodiments of the present invention have been described above in detail, it will be understood that this description is merely for purposes of illustration. Specific features of the invention are shown in some drawings and not in others; this is for convenience only, and any feature may be combined with another in accordance with the invention. Further variations will be apparent to one skilled in the art in light of this disclosure, for example, the apparatus may comprise a specialized plunger instead of being used in conjunction with a standard brachytherapy plunger, and all such variations are intended to fall within the scope of the appended claims.

What is claimed is:

1. Apparatus for loading therapeutic materials into brachytherapy needles comprising:
    a loading channel with proximal and distal ends, the loading channel configured to accept a column of radioactive seeds and spacers;
    a first cartridge comprising a plurality of seed chambers, the first cartridge disposed to slidably intersect the loading channel between the proximal and distal ends; and
    a second cartridge comprising a plurality of spacer chambers, the second cartridge disposed to slidably intersect the loading channel between the proximal and distal ends.

2. The apparatus of claim 1 further comprising a plunger configured for reciprocation in the loading channel.

3. The apparatus of claim 1 further comprising means for retaining a spacer in each one of the plurality of spacer chambers.

4. The apparatus of claim 1 further comprising means for retaining a radioactive seed in each one of the plurality of seed chambers.

5. The apparatus of claim 1 wherein the distal end of the loading channel is adapted to be coupled to a brachytherapy needle.

6. The apparatus of claim 1 wherein the first and second cartridges are configured to be manually reciprocated relative to the loading channel.

7. The apparatus of claim 1 wherein the first cartridge is fabricated from a shielding material.

8. The apparatus of claim 7 wherein the shielding material is lead.

9. The apparatus of claim 1 wherein the first and second cartridges are fabricated from a transparent or translucent material.

10. The apparatus of claim 1 wherein the first cartridge intersects the loading channel at a location axially offset from the second cartridge.

11. A method for loading therapeutic materials into brachytherapy needles comprising:
    providing apparatus comprising a loading channel with proximal and distal ends, a first cartridge comprising a plurality of seed chambers loaded with radioactive seeds, the first cartridge slidably intersecting the loading channel, a second cartridge comprising a plurality of spacer chambers loaded with spacers, the second cartridge slidably intersecting the loading channel, a plunger, and a brachytherapy needle;
    coupling the distal end of the loading channel to the brachytherapy needle;
    inserting a distal end of the plunger within the loading channel;
    distally advancing the plunger relative to the loading channel to advance a radioactive seed or a spacer from a cartridge chamber aligned with the loading channel; and
    advancing the plunger relative to the loading channel to advance a column of seeds and spacers into the brachytherapy needle.

12. The method of claim 11 further comprising proximally retracting the plunger.

13. The method of claim 12 further comprising sliding the cartridges relative to the loading channel to align subsequent seeds and spacers with the loading channel.

14. The method of claim 13 further comprising loading the needle with seeds and spacers in a predetermined packing arrangement.

15. Apparatus for loading therapeutic materials into brachytherapy needles comprising:
    a loading channel having proximal and distal ends;
    first and second cartridges disposed to slidably intersect the loading channel, the first and second cartridges comprising a plurality of first and second chambers, respectively; and
    a plunger disposed for reciprocation within the loading channel.

16. The apparatus of claim 15 further comprising means for retaining a spacer in each one of the plurality of second chambers.

17. The apparatus of claim 15 further comprising means for retaining a radioactive seed in each one of the plurality of first chambers.

18. The apparatus of claim 15 wherein the distal end of the loading channel is adapted to be coupled to an interior lumen of a brachytherapy needle.

19. The apparatus of claim 15 wherein the first and second cartridges are configured to be manually reciprocated relative to the loading channel.

20. The apparatus of claim 15 wherein the first cartridge is fabricated from a shielding material.

* * * * *